(12) United States Patent
Kim

(10) Patent No.: US 12,033,745 B2
(45) Date of Patent: Jul. 9, 2024

(54) OPTIMIZED SHIPBOARD TELEHEALTH

(71) Applicant: Royal Caribbean Cruises Ltd., Miami, FL (US)

(72) Inventor: Eunha Kim, Miami, FL (US)

(73) Assignee: Royal Caribbean Cruises, Ltd., Miami, FL (US)

( * ) Notice: Subject to any disclaimer, the term of this patent is extended or adjusted under 35 U.S.C. 154(b) by 439 days.

(21) Appl. No.: 17/209,195

(22) Filed: Mar. 22, 2021

(65) Prior Publication Data

US 2022/0301696 A1 Sep. 22, 2022

(51) Int. Cl.
| | |
|---|---|
| *G16H 40/20* | (2018.01) |
| *G01C 21/20* | (2006.01) |
| *G06F 3/0482* | (2013.01) |
| *G16H 40/67* | (2018.01) |
| *H04W 4/024* | (2018.01) |
| *H04W 4/029* | (2018.01) |

(52) U.S. Cl.
CPC ........... *G16H 40/20* (2018.01); *G01C 21/206* (2013.01); *G16H 40/67* (2018.01); *H04W 4/024* (2018.02); *H04W 4/029* (2018.02); *G06F 3/0482* (2013.01)

(58) Field of Classification Search
CPC ...... G16H 40/20; G16H 40/67; G01C 21/206; G01C 21/203; H04W 4/024; H04W 4/029; G06F 3/0482
See application file for complete search history.

(56) References Cited

U.S. PATENT DOCUMENTS 11,410,091 B2 * 8/2022 Renganathan ........ G06T 19/006
11,682,058 B1 * 6/2023 Shmulyan .......... G06Q 30/0639
705/26.2

(Continued)

FOREIGN PATENT DOCUMENTS

WO WO-2021217139 A1 * 10/2021 ......... G06Q 30/0601

OTHER PUBLICATIONS

"How Cruise Lines are Preparing for a Post-Pandemic World". Retrieved from <https://maritime-executive.com/features/how-cruise-lines-are-preparing-for-a-post-pandemic-world>. Sep. 2020. (Year: 2020).*

(Continued)

*Primary Examiner* — Nathan A Mitchell
(74) *Attorney, Agent, or Firm* — CRGO Global; Steven M. Greenberg

(57) ABSTRACT

Embodiments of the present invention provide a method, system and computer program product for optimized shipboard health. In an embodiment of the invention, a method for optimized shipboard health includes first registering different mobile devices, each for a different passenger on an oceangoing vessel. Then, the state of each of different PPE dispensaries on board the vessel may be monitored, including a supply of PPE at each of the dispensaries and a number of passengers present at each of the dispensaries. Thereafter, in response to a request by one of the passengers received by way of a corresponding mobile device, a listing may be presented, in a user interface of the mobile device, of one or more dispensaries each having both a monitored threshold level of supply of the PPE and also less than a monitored threshold number of the passengers present at the dispensary.

15 Claims, 2 Drawing Sheets

(56) References Cited

U.S. PATENT DOCUMENTS

| | | | | |
|---|---|---|---|---|
| 2005/0097005 | A1* | 5/2005 | Fargo | G06Q 30/00 |
| | | | | 705/26.62 |
| 2012/0117047 | A1* | 5/2012 | Xu | G06F 16/951 |
| | | | | 707/706 |
| 2015/0371152 | A1* | 12/2015 | Rubsamen | G06Q 10/087 |
| | | | | 705/5 |
| 2017/0193431 | A1* | 7/2017 | Grams | G06F 16/24573 |
| 2018/0107738 | A1* | 4/2018 | Xu | G06Q 10/087 |
| 2021/0007179 | A1* | 1/2021 | Levy | H04W 84/18 |
| 2022/0147881 | A1* | 5/2022 | Renganathan | G06Q 10/109 |

OTHER PUBLICATIONS

Schlaich, Clara, et al. "Infection control measures on ships and in ports during the early stage of pandemic influenza A (H1N1) 2009." International Maritime Health 63.1 (2012): 17-23. (Year: 2012).*

Ilapakurti, Anitha, et al. "iDispenser—big data enabled intelligent dispenser." 2017 IEEE Third International Conference on Big Data Computing Service and Applications (BigDataService). IEEE, 2017. (Year: 2017).*

\* cited by examiner

OPTIMIZED SHIPBOARD TELEHEALTH

BACKGROUND OF THE INVENTION

Field of the Invention

The present invention relates to the field of telehealth and more particularly to managing telehealth on an oceangoing vessel.

Description of the Related Art

Telehealth refers to the distribution of health-related services and information via electronic information and telecommunication technologies. In this regard, telehealth allows long-distance patient and clinician contact, care, advice, reminders, education, intervention, monitoring, and remote admissions. In the case where ready access to the facilities of a health care provider, telehealth may bridge the gap. Indeed, even where a health care provider can be accessed, but not the health care provider already providing health care to a patient, telehealth can allow for the continuity of care between a patient and physician. So much is particularly true whilst the patient vacations in a location remote from the home of the patient.

In this regard, when vacationing in a different state or country, should the need arise, a vacationer can access health care support locally. Examples include acquiring medicine and health care supplies at a pharmacy, visiting an emergency room or visiting an urgent care facility. The abundance of such facilities far outstrips the demand. But in certain vacation settings, so much is not the case. For example, when vacationing with a cruise line on an oceangoing vessel, there is but one pharmacy and one health care clinic available to serve all of the passengers, which in an era modern cruising, can number several thousand. As well, unique considerations can arise in the context of a cruise ship, such as maintaining an adequate inventory of health care supplies at distribution points about the vessel, and avoiding crowded areas at the points of delivery of health care services aboard the vessel, especially when seeking to reduce the spread of illness.

BRIEF SUMMARY OF THE INVENTION

Embodiments of the present invention address deficiencies of the art in respect to telehealth in a cruise ship and provide a novel and non-obvious method, system and computer program product for optimized shipboard health. In an embodiment of the invention, a method for optimized shipboard health includes first registering different mobile devices, each for a different passenger on an oceangoing vessel. Then, the state of each of different PPE dispensaries on board the vessel may be monitored, including a supply of PPE, such as hand sanitizer or respiratory masks, at each of the dispensaries and a number of passengers present at each of the dispensaries. Thereafter, in response to a request by one of the passengers received by way of a corresponding mobile device, a listing may be presented, in a user interface of the mobile device, of one or more dispensaries each having both a monitored threshold level of supply of the PPE and also less than a monitored threshold number of the passengers present at the dispensary.

In one aspect of the embodiment, the corresponding one of the registered different mobile devices may be located on the vessel and the listing then can be sorted in accordance with a nearest one of the corresponding one of the dispensaries nearest to the located corresponding one of the registered different mobile devices. Likewise, the corresponding mobile device may be located on the vessel, a route computed from the located mobile device to the dispensary nearest to the located mobile device and the route than can be displayed in the user interface.

In another embodiment of the invention, a data processing system may be adapted for optimized shipboard health. The system includes a host computing platform that has one or more computers, each with memory and at least one processor. The system also includes an optimized shipboard health module. The module includes computer program instructions enabled while executing in the host computing platform to register different mobile devices, in a data store of the host computing platform, each for one of a multiplicity of different passengers on an oceangoing vessel. The instructions are further enabled to monitor a state of each of different PPE dispensaries on board the vessel including a supply of PPE at each of the dispensaries and a number of passengers present at each of the dispensaries. Finally, the program instructions are enabled to respond to a request by one of the passengers received by way of a corresponding one of the registered different mobile devices, by presenting in a user interface of the corresponding one of the registered different mobile devices a listing of dispensaries each corresponding one of the dispensaries in the listing having a monitored threshold level of supply of the PPE and having less than a monitored threshold number of the passengers present at the corresponding one of the dispensaries in the listing.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for optimized shipboard health. In accordance with an embodiment of the invention, different mobile devices for different passengers on an oceangoing vessel are registered with a data processing system and different PPE dispensaries onboard the vessel are monitored for both supply level and number of passengers proximate thereto. Then, upon receiving a request for PPE, such as hand sanitizer or disposable masks, from one of the mobile devices, the mobile device is geolocated onboard the vessel and a nearest one of the PPE dispensaries, both having a threshold supply of PPE and also an acceptable level of crowdedness below a threshold, is displayed in the mobile device. Optionally, a routing to the nearest one of the PPE dispensaries from the location of the mobile device is presented in the mobile device. In this way, passengers onboard the vessel, on demand, can access PPE in an optimized way while avoiding crowds and assuring an ample supply of the desired PPE.

Figure 1:
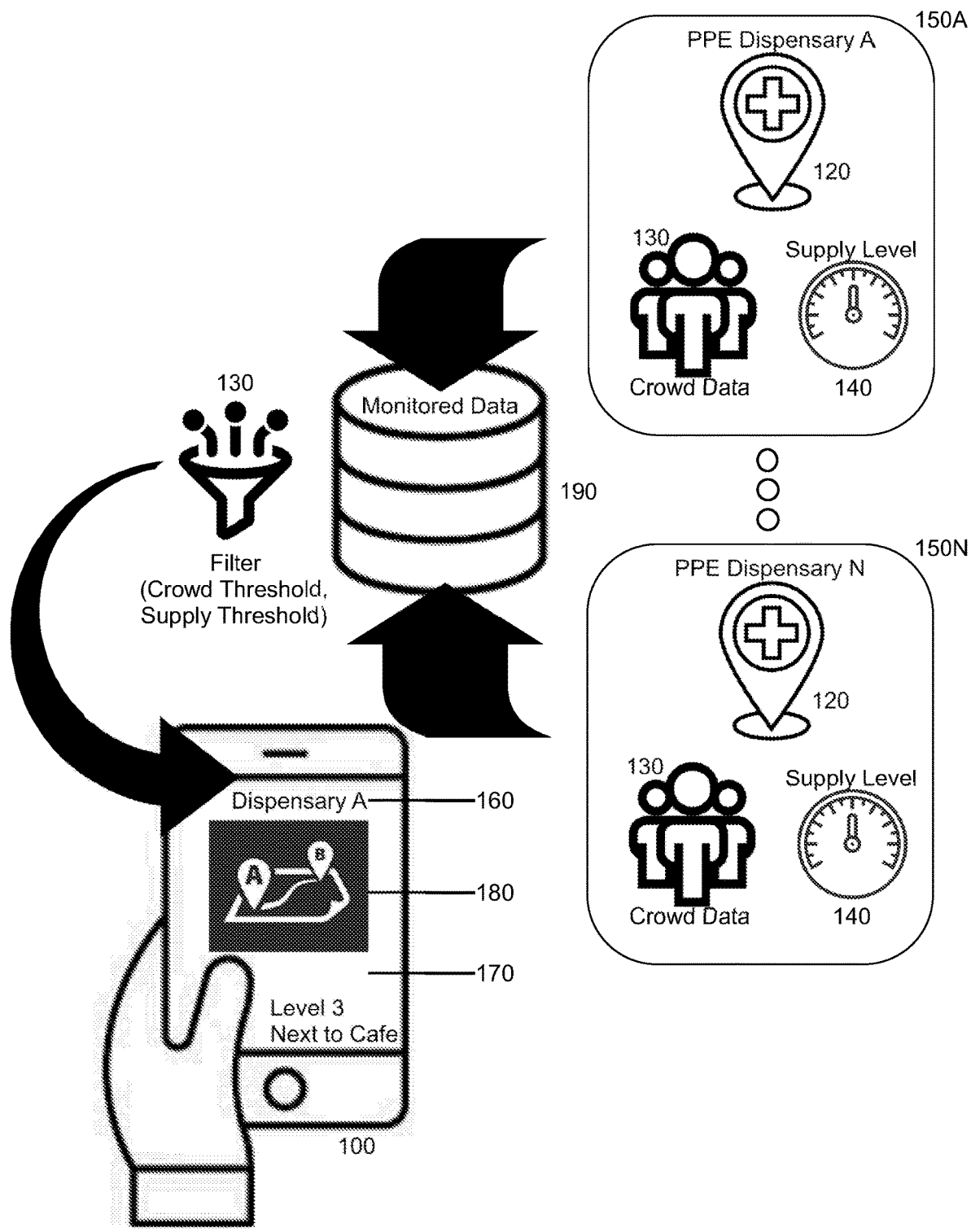
FIG. 1 is pictorial illustration of a process for optimized shipboard health.

In further illustration, FIG. 1 is pictorial illustration of a process for optimized shipboard health. As shown in FIG. 1, a request for PPE, such as a respiratory mask or hand sanitizer, can be initiated from a mobile device 100. In response, a location of the mobile device 100 can be determined and a data store of monitored data 190 can be consulted in order to identify a state 150A, 150N of each of different corresponding PPE dispensaries 120 on board the vessel. Of import, the state 150A, 150N includes both a crowdedness determination 130 of the crowdedness of the corresponding dispensary 120, and a supply level 140 of PPE at the corresponding dispensary 120.

Thereafter, a filter 130 is applied to the state 150A, 150N for each corresponding dispensary 120 in order to create a subset listing of dispensaries 120 having a threshold supply level 140 and no more than a threshold degree of crowdedness 130. Dispensaries 120 with a degree of crowdedness 130 exceeding a threshold value, and those of the dispensaries 120 with less than a threshold value of supply level 140 are excluded from the subset listing. Finally, the subset is presented a user interface 170 to the mobile device 100. Upon selection of one 160 of the dispensaries 120 in the user interface 170, a routing 180 can be computed as between the determined location of the mobile device 100 and the selected one 160 of the dispensaries 120, and presented in the user interface 170 of the mobile device 120.

Figure 2:
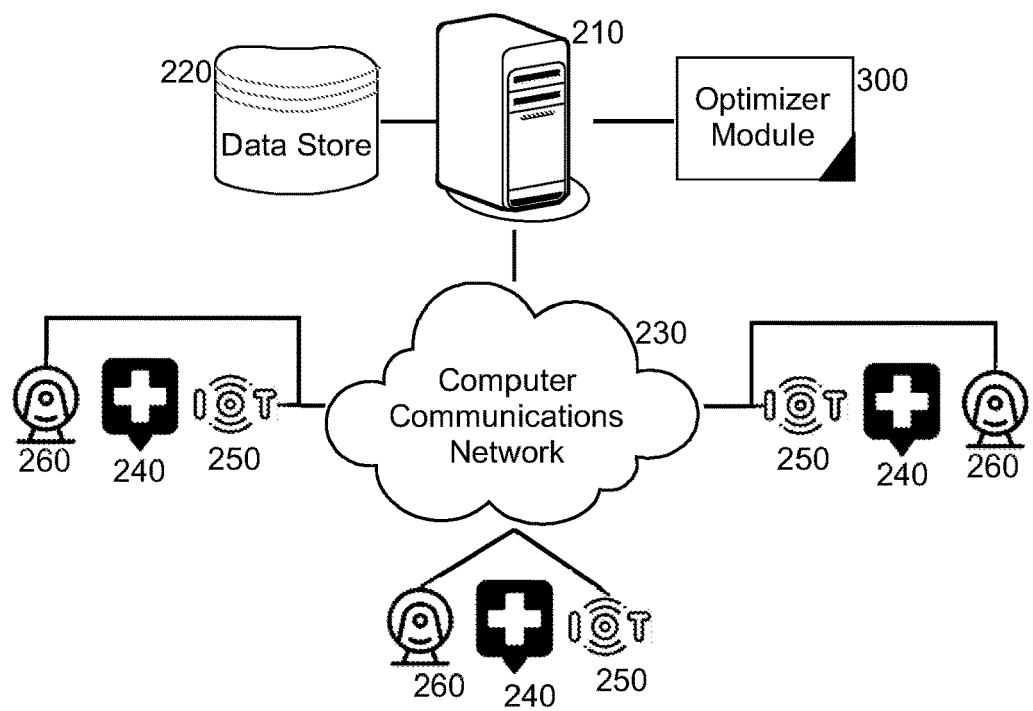
FIG. 2 is a schematic diagram of an onboard data processing system configured for optimized shipboard health; and, FIG. 3 is a flow chart illustrating a process for optimized shipboard health.

The process described in connection with FIG. 1 can be implemented in a data processing system. In yet further illustration, FIG. 2 schematically shows an onboard data processing system configured for optimized shipboard health. The system includes a host computing platform 210 that includes one or more computers, each with memory and at least one processor. The host computing platform 210 is communicatively coupled over computer communications network 230 to a multiplicity of different Internet of Things (IoT) enabled sensors 250 positioned at different corresponding dispensaries 240. Each of the IoT enabled sensors 260 is adapted to receive an indication of supply level of PPE at a corresponding one of the dispensaries 240. The indication of supply level of PPE can be manually specified at an input device of a corresponding one of the IoT enabled sensors 250, or the indication of supply level of PPE can be automatically determined through an optical sensor sensing a level of product such as hand sanitizer or masks, or a float sensor sensing a level of product, to name two possible examples.

A camera 260 also can be positioned at each of the dispensaries 240 and communicatively coupled to the host computing platform 230 by way of the computer communications network 230. Each camera 260 can provide imagery of a corresponding one of the dispensaries 240 from which a degree of crowdedness can be ascertained. The degree of crowdedness can be determined at the camera 260 and the resulting value transmitted to the host computing platform 210, or the image itself can be transmitted to the host computing platform 210 and the degree of crowdedness can be determined at the host computing platform 210.

Importantly, the system can include an optimizer module 300. The optimizer module 300 includes computer program instructions that when executing in the memory of the host computing platform 210, maintains a data store 220 of status information for each of the dispensaries 240, including a supply level determined from a corresponding one of the IoT devices 250, and crowdedness determined from imagery from a corresponding one of the cameras 260. The program instructions further respond to requests from mobile devices for PPE access by filtering a list of the dispensaries 240 to only those of the dispensaries 240 having a minimum threshold of supply of PPE and less than a maximum permitted crowdedness. Then, the program instructions can sort the filtered list either by distance from each requesting one of the mobile devices, or by least crowded one of the dispensaries 240 within a threshold distance of the requesting one of the mobile devices. Optionally, the program instructions can compute a routing from a requesting one of the mobile devices to a selected one of the dispensaries 240 for display in a user interface to the requesting one of the mobile devices.

Figure 3:
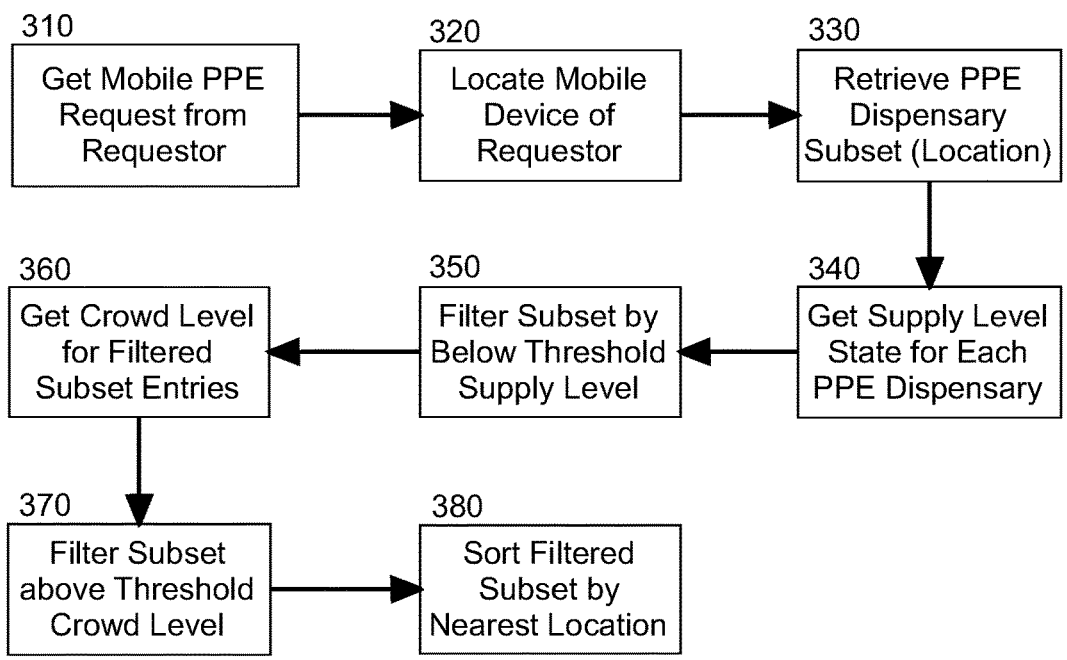

In even yet further illustration of the operation of the optimizer module 300, FIG. 3 is a flow chart illustrating a process for optimized shipboard health. Beginning in block 310, a mobile PPE request is received from a mobile device of a requestor. In block 320, a location of the mobile device is determined, either by global positioning or by association to a wireless access point of fixed location. In block 330, a dispensary subset is retrieved from a data store at which the requested PPE is dispensed. Then, in block 340, a supply level is determined from a record in the data store for each dispensary in the subset. As such, in block 350, the subset is filtered to remove therefrom dispensaries with inadequately low supply levels. Thereafter, in block 360 a degree of crowdedness is determined from the record in the data store for each of the dispensaries in the filtered subset and in block 370, the filtered subset is filtered once again to remove therefrom any dispensary with a crowdedness that exceeds a maximum permitted level. Finally, in block 380 the twice filtered subset is sorted according to location nearest the mobile device and presented in a user interface of the requesting mobile device.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "include", "includes", and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

I claim:

1. A method for optimized shipboard health, comprising:
registering different mobile devices, in a data store of a computer, each for one of a multiplicity of different passengers on an oceangoing vessel;
monitoring a state of each of different personal protective equipment (PPE) dispensaries on board the vessel including a supply of PPE at each of the dispensaries by receiving an indication of a supply level of a dispenser of the PPE from an optical sensor sensing the supply level, and a number of passengers present at each of the dispensaries by processing imagery from a camera into a degree of crowdedness; and,
responsive to a request by one of the passengers received by way of a corresponding one of the registered different mobile devices, presenting in a user interface of the corresponding one of the registered different mobile devices a listing of dispensaries each corresponding one of the dispensaries in the listing having a monitored threshold level of supply of the PPE and having less than a monitored threshold number of the passengers present at the corresponding one of the dispensaries in the listing.

2. The method of claim 1, further comprising:
locating the corresponding one of the registered different mobile devices on the vessel; and,
sorting the listing in accordance with a nearest one of the corresponding one of the dispensaries nearest to the located corresponding one of the registered different mobile devices.

3. The method of claim 1, further comprising:
locating the corresponding one of the registered different mobile devices on the vessel;
computing a route from the located one of the corresponding one of the registered different mobile devices to a nearest one of the corresponding one of the dispensaries nearest to the located corresponding one of the registered different mobile devices; and,
displaying the route in the user interface.

4. The method of claim 1, wherein the PPE dispensaries dispense hand sanitizer.

5. The method of claim 1, wherein the PPE dispensaries dispense respiratory masks.

6. A data processing system adapted for optimized shipboard health, the system comprising:

a host computing platform comprising one or more computers, each comprising memory and at least one processor; and, an optimized shipboard health module comprising computer program instructions enabled while executing in the host computing platform to perform:

registering different mobile devices, in a data store of the host computing platform, each for one of a multiplicity of different passengers on an oceangoing vessel;

monitoring a state of each of different personal protective equipment (PPE) dispensaries on board the vessel including a supply of PPE at each of the dispensaries by receiving an indication of a supply level of a dispenser of the PPE from an optical sensor sensing the supply level, and a number of passengers present at each of the dispensaries by processing imagery from a camera into a degree of crowdedness; and, responsive to a request by one of the passengers received by way of a corresponding one of the registered different mobile devices, presenting in a user interface of the corresponding one of the registered different mobile devices a listing of dispensaries each corresponding one of the dispensaries in the listing having a monitored threshold level of supply of the PPE and having less than a monitored threshold number of the passengers present at the corresponding one of the dispensaries in the listing.

7. The system of claim 6, wherein the program instructions further perform:

locating the corresponding one of the registered different mobile devices on the vessel; and, sorting the listing in accordance with a nearest one of the corresponding one of the dispensaries nearest to the located corresponding one of the registered different mobile devices.

8. The system of claim 6, wherein the program instructions further perform:

locating the corresponding one of the registered different mobile devices on the vessel;

computing a route from the located one of the corresponding one of the registered different mobile devices to a nearest one of the corresponding one of the dispensaries nearest to the located corresponding one of the registered different mobile devices; and, displaying the route in the user interface.

9. The method of claim 6, wherein the PPE dispensaries dispense hand sanitizer.

10. The system of claim 6, wherein the PPE dispensaries dispense respiratory masks.

11. A computer program product for optimized shipboard health, the computer program product including a computer readable storage medium having program instructions embodied therewith, the program instructions executable by a device to cause the device to perform a method including:

registering different mobile devices, in a data store of a computer, each for one of a multiplicity of different passengers on an oceangoing vessel;

monitoring a state of each of different personal protective equipment (PPE) dispensaries on board the vessel including a supply of PPE at each of the dispensaries by receiving an indication of a supply level of a dispenser of the PPE from an optical sensor sensing the supply level, and a number of passengers present at each of the dispensaries by processing imagery from a camera into a degree of crowdedness; and, responsive to a request by one of the passengers received by way of a corresponding one of the registered different mobile devices, presenting in a user interface of the corresponding one of the registered different mobile devices a listing of dispensaries each corresponding one of the dispensaries in the listing having a monitored threshold level of supply of the PPE and having less than a monitored threshold number of the passengers present at the corresponding one of the dispensaries in the listing.

12. The computer program product of claim 11, wherein the method further includes:

locating the corresponding one of the registered different mobile devices on the vessel; and, sorting the listing in accordance with a nearest one of the corresponding one of the dispensaries nearest to the located corresponding one of the registered different mobile devices.

13. The computer program product of claim 11, wherein the method further includes:

locating the corresponding one of the registered different mobile devices on the vessel;

computing a route from the located one of the corresponding one of the registered different mobile devices to a nearest one of the corresponding one of the dispensaries nearest to the located corresponding one of the registered different mobile devices; and, displaying the route in the user interface.

14. The computer program product of claim 11, wherein the PPE dispensaries dispense hand sanitizer.

15. The computer program product of claim 11, wherein the PPE dispensaries dispense respiratory masks.

* * * * *